United States Patent
Lawson

(10) Patent No.: US 6,443,572 B1
(45) Date of Patent: Sep. 3, 2002

(54) METHOD AND APPARATUS FOR TREATING DYSLEXIA

(76) Inventor: Alison Marie Lawson, "Rotherfield", Holly Road, Burradoo, NSW 2576 (AU)

(*) Notice: Subject to any disclaimer, the term of this patent is extended or adjusted under 35 U.S.C. 154(b) by 0 days.

(21) Appl. No.: 09/405,755

(22) Filed: Sep. 27, 1999

(51) Int. Cl.[7] ................................................. A61B 3/00
(52) U.S. Cl. ...................................................... 351/203
(58) Field of Search .................................. 351/200, 201, 351/202, 203, 237, 238, 243, 246; 606/204.25

(56) References Cited

U.S. PATENT DOCUMENTS 3,955,564 A * 5/1976 Lrvinson et al. ....... 606/204.25
5,007,838 A    4/1991 Cochran

OTHER PUBLICATIONS

Article entitled The magnocellular deficit hypothesis in dyslexia: a review of reported evidence, by J.C. Greatrex and N. Drasdot, *Ophthal. Physiol. Opt.*, vol. 15, No. 5, pp. 50–1506, 1995.

* cited by examiner

Primary Examiner—George Manuel
(74) Attorney, Agent, or Firm—Fulwider, Patton Lee & Utecht, LLP

(57) ABSTRACT

A method for treating Dyslexia in a patient, the method comprising the step of employing techniques to achieve a stable fixation of both eyes.

11 Claims, 9 Drawing Sheets

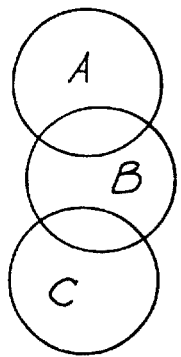

FIG. 13

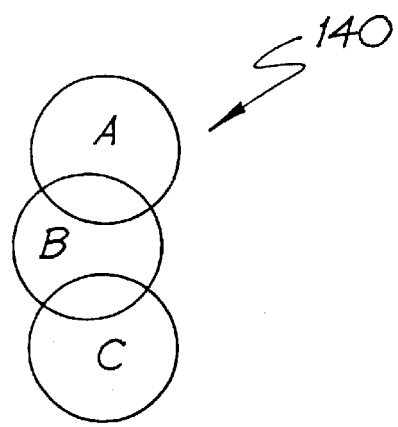

vary ing the
dis tance in
the stereoscope. ◐
   The Charts in
series G should al-
ways be preceded
by the series F
which are more
artfully designed.

vary ing thé
dis tance in
the stereoscope. ⊜
   The Charts in
series G should al-
ways be preceded
by the series F
which are more
artfully designed.

FIG. 14 are cöm-
bıned to
˙obt⸌ in
binôcular
⁄ision.

are cöm-
bined˝ to
obtaın
bınocular
ᴠision.

FIG. 15

METHOD AND APPARATUS FOR TREATING DYSLEXIA

FIELD OF THE INVENTION

The present invention relates to a method and device for the treatment of conditions such as Dyslexia.

BACKGROUND OF THE INVENTION

Dyslexia is a term used to denote a condition of reduced ability to read and write, in the presence of adequate intelligence, conventional instruction and sociocultural opportunity and without any opthalmoscopically detectable retinal abnormality. A proportion of those with this condition also display an inability to listen in the absence of any impairment in their hearing.

The several manifestations of this condition have been encapsulated in the term 'Dyslexia', derived from the Greek 'dys'—meaning difficult, and 'lexis'—meaning words. A common expression describes 'Dyslexia' as 'word blindness.'

The condition was first noticed in the 1860's in some patients who had suffered a brain injury. It was later uncovered that the condition was more typically present without brain injury and in far greater numbers than expected.

Some estimates suggest that Dyslexia is present in about fifteen percent of the World population to some degree.

For the untrained person, Dyslexia is difficult to detect. Teachers unskilled in the identification of Dyslexia may misdiagnose children to be lazy, forgetful, inattentive and unintelligent. For this reason, the British Dyslexia Association refers to Dyslexia as the 'hidden handicap' because the condition is not obvious to all but the trained.

Chronic academic under achievement, sporting ineptitude and an apparent bumbling nature conspire to form an ingrained loss of self-esteem for the youthful Dyslexic. Later for some, this may develop into anti-social behaviour. Others become suicidal. For all, it is often a lifetime of unjust treatment and a failure to reach potential as an individual.

Although it is difficult to quantify, it is clear that a condition as elusive, pervasive and pernicious as Dyslexia must impose heavy social and economic costs. The British Dyslexia Association says that "Dyslexia cannot be prevented or cured, but by teaching appropriate skills and strategies necessary for learning and life, the problems it causes in and out of school can be eased."Despite an appellation suggestive of visual disorder, Dyslexia became most often attributed to auditory causes. Hence remediations of the past commonly employed methods and inventions that were based upon phonetic techniques. Some clinics to the current date still are based on the assumption of auditory causes.

In recent years, more searching diagnostic techniques have uncovered differences in the sectors of the brain utilised by Dyslexics for purposes of reading. Dyslexics do not appear to fully use their magnocellular pathways, which had evolved to better process fast moving, low contrast objects.

The frontal lobes of the brain in Dyslexics also revealed a greater activity during reading and writing than in non-Dyslexics.

Autopsies have confirmed that the magnocellular pathways are debilitated in Dyslexics, by revealing smaller, fewer pathway cells, and greater disorganisation in the layers of the visual cortex.

The reaction of those in the profession of treating Dyslexia appears mixed in regard to the scientific findings of a strong visual element to the condition of Dyslexia:

Some, whose treatment was based on an assumption of auditory causes, continued to promote the phonological path as that most preferred. Some, whose treatment was to teach alternative methods of reading that did not depend upon an accurate visual perception of what was written, continued their compensatory approach. Others sought to better utilise the debilitated visual pathways of Dyslexics, by filtering light difficult for these pathways to transmit.

All such treatments for Dyslexia are either essentially palliative in nature or have the objectives of developing compensatory behaviour.

SUMMARY OF THE INVENTION

In accordance with a first aspect of the present invention, there is provided a method for treating Dyslexia in a patient, the method comprising the step employing techniques to achieve a stable fixation of both eyes.

The method may comprise the step of employing techniques to strengthen the magnocellular visual pathways of the patient.

In one embodiment, the method comprises utilising a series of visual image exercises provided so as to achieve the stable fixation and to strengthen the magnocellular visual pathways.

The visual images can comprise one or more series of high frequency striations interposed with a visual work exercise exercising the patient mental faculties.

The visual work exercise can include, for example, one of a puzzle, a drawing or a story.

The visual work exercises are preferably of increasing mental complexity.

In a further modification, the step can further comprise occluding one of the patients eyes during the visual image exercise and/or colour filtering the light transmitted to the patients eyes during the visual image exercise. Preferably a red filter is utilised.

The present invention is different to all known prior treatments for Dyslexia, in that it seeks to address the causes of Dyslexia. The present invention has been developed as a result of extensive observations of those displaying the symptoms of Dyslexia in that they are unable to hold a steady fixation on the fovea. Usually there is a fixation drift in at least one eye. The magnitude of this fixation drift was found to be usually less than that observed for Strabismus or Amblyopia, and again unlike Strabismus and Amblyopia, the fixation was almost always in motion, away from and back again to the fovea, seeming to drift in sympathy with the patient's level of concentration or fatigue.

With the knowledge that a larger fixation error causes the Diplopia of Strabismus or the suppression of one eye in Amblyopia, the inventor has deduced that it is the smaller, constantly moving fixation drift of Dyslexics that causes lack of concentration whether listening to a techer or reading.

This phenomenon may be related to the condition commonly described as 'word blindness', which concurs with the numerous descriptions given by Dyslexics themselves when they talk of their affliction in their own words 'of letters and words disappearing off the page'.

Further, the physical act of reading requires the eyes to scan a stream of symbols varying in fine detail, with speed, accuracy and consistency, and this requires a speed of vision perception for which fully functional magnocellular pathways are essential but are debilitated in Dyslexics.

The resulting method of treatment helps restore functionality to the magnocellular visual pathway systems by forcing them to be utilised in escalating degrees of difficulty.

It is noted here that in the context of this specification it is not intended to limit the present invention to a treatment of Dyslexia only, but rather to the treatment of the particular visual element of Dyslexia, which has been found by the applicants to be the key element of Dyslexia. As such, it will be appreciated by a person skilled in the art that e.g. the treatment of Attention Deficit Disorder (ADD) does also fall within the scope of the present invention where the key element of the condition has been found to be substantially the same visual element as described for Dyslexia hereinbefore.

In that regard, it is further noted that medical terms such as Dyslexia are often interpreted differently by different persons in the medical field, which is a further reason why limitation of the scope of the present invention as per a particular interpretation of the term Dyslexia is not appropriate. Also, the medically same condition may be referred to in praxis by different names in for example different countries.

BRIEF DESCRIPTION OF THE DRAWINGS

In order that the invention may be more fully understood an apparatus embodying the invention will now be described with the assistance of the accompanying drawings wherein:

FIG. 13 illustrates an ABC card for use with the method of the preferred embodiment;

FIGS. 14 and 15 illustrates two fine print stereogram for utilisation with the method of the preferred embodiment.

DESCRIPTION OF THE PREFERRED AND OTHER EMBODIMENTS

Figure 1:
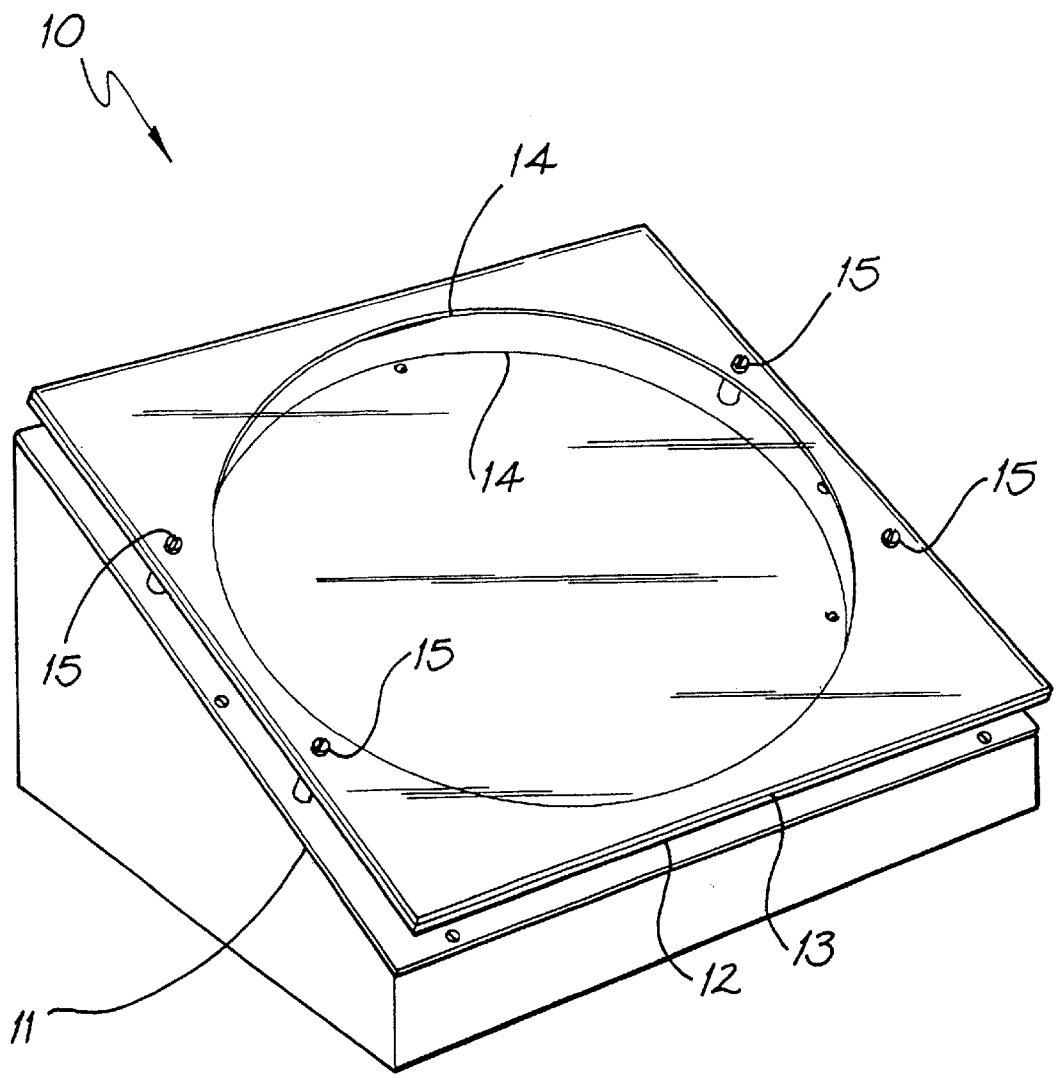
FIG. 1 is a perspective view of an apparatus for use in a method embodying the present invention.

The implementation of the preferred embodiment is a consequence of the discovery that the signature for visual Dyslexia is the unstable focus of one eye. This in turn can be cured by a series of high contrast striations, in combination with interposed exercises and further assisted by occlusion or/and colour filtering. To make the stable focus permanent and to give the visual system an ability to scan symbols rapidly as is normally essential for reading requires the strengthening of the magnocellular visual pathways. This is provided by interposed exercises that cognitively extend the patient.

The method of treatment can proceed by utilising an apparatus disclosed below. This apparatus can comprise an open sided housing provided internally with illumination means, and arranged to accept any one of a series of generally planar transparencies for location and rotation in or adjacent to the plane containing the open side. The transparencies comprise a series of opaque striations of varying but particular width and spacing. Through the transparent spacing between the striations, illumination of a reasonably even degree is arranged from within the housing. For the purposes of this apparatus, the circular transparencies shall be described as stimulation discs. The motor apparatus arranged for rotating the stimulation discs is in its own plane.

The drive for the motor apparatus in this apparatus is at the outer circumference of the stimulation discs. This 'centerless drive' requires that the stimulation disc is stiff and adequately round, with outer guides to enable the centre of rotation to be fixed at the centre of the stimulation disc but without the distraction of visible drive shafts.

An advantage of the centerless drive configuration is that the rotating striations occur in the important area in the vision of the patient—the centre of focus. A further advantage of this 'centerless drive' configuration, is that it enables the ejection and therefore removal of the stimulation discs to be arranged by means of an ejection arm mounted to the housing in the plane of the transparency, enabling the movement of the stimulation discs laterally away from the circumferential support wheels, in the plan of rotation.

Another advantage of this 'centerless drive' configuration is that it more easily enables two further transparent sheets to be mounted close to and parallel to the stimulation discs, but separated sufficiently to allow the insertion of a further transparency.

In the case where the apparatus is used for the treatment of Dyslexia such transparencies also provide the primary role of rehabilitating the magnocellular pathways. This outcome is sought by the methodical background stimulation provided by the apparatus, over which a controlled cognitive exertion regime is provided by means of particular transparencies called Targets.

Though the reasonably even illumination of the stimulation discs and the Targets may be effected by any known method, it is preferable that a plurality of fluorescent tubes be mounted within the housing, the internal walls of which are coated with a light reflective substance, and that a translucent sheet of material, such as opalescent diffuser, be interposed between the light emitting from the housing and the two transparent sheets that provide the supporting space for the various Targets. Further, extra light reflective surfaces may be provided within the housing in the order to achieve the required light dispersion over the stimulation discs and the targets.

Preferably, the transparencies providing the supporting space for the Targets be made from glass, although rigid acrylic type plastic sheets may suffice. Similarly it is preferable that the Targets themselves are also made from glass, although thin plastic sheet with good transparent properties may also suffice.

In the preferred case the apparatus embodying the invention is provided in a housing with a base dimension about 330 mm by about 350 mm.

The present invention displays several advantages, which are itemised below:

1. The rotating stimulation discs are more than double the diameter and therefore more than four times the area of those in prior art, thereby enhancing the effectiveness of the treatment by this invention, both through the minimisation of distracting peripheral vision and by broadening the field of visual cortex stimulation.
2. The rotating stimulation discs have a 'centerless drive' configuration which introduces rotating striations where previously there were none, and into the important area in the vision of the patient—the centre of focus.
3. The 'centerless drive' configuration allows only the rotating stimulation discs themselves to be easily and quickly replaced, thereby minimising the disruption time during treatment, which if occurring at times at or near the peak of cognitive exertion, is particularly advantageous to avoid.
4. The provision of effective and well diffused back lighting in the visual components of the stimulation discs and Target transparency combinations, provide good stimulation to the debilitated cells of the visual magnocellular pathways.
5. Having an initial treatment with this invention of occluding the good eye and placing a red filter over the eye with fixation instability, is effective in restoring fixation stability and in stimulating the debilitated magnocellular pathways.
6. The treatment subsequent to 5), where no occlusion is employed and the red filter is placed over the good eye, is more effective in that it allows the treatment to proceed with binocular vision whilst preventing a regression to the compensatory visual behaviour of the dominant good eye, and at the same time achieving bimacular fixation stability, which is important in the treatment of Dyslexia.

The use of this apparatus together with treatments as in 5) & 6), together with transparencies designed to maximise cognitive exertion, giving due consideration to age, gender, aptitude, experience, interest, degree and extent of visual pathway debilitation, provides a degree of effectiveness in the treatment of Dyslexia.

One form of apparatus suitable for utilization with the method of the preferred embodiment will now be described with reference to the figures.

Looking first to FIG. 1, the perspective view of the apparatus of the preferred embodiment shows a housing 10 to which is fitted a translucent sheet of acrylic 11, a sheet of transparent glass 12 and a transparent acrylic covering sheet 13. The glass sheet 12 and acrylic sheet 11 are both provided with a transparent aperture centrally of the sheets and indicated by perimeter line 14. The rest of these two sheets is "blacked out". While sheet 11 is mounted flush with the plane containing the open side of the housing, sheets 12 and 13 are mounted parallel with that plane, though offset therefrom and mounted in the offset position on a plurality of supported positioned as indicated at 15.

Figure 2:
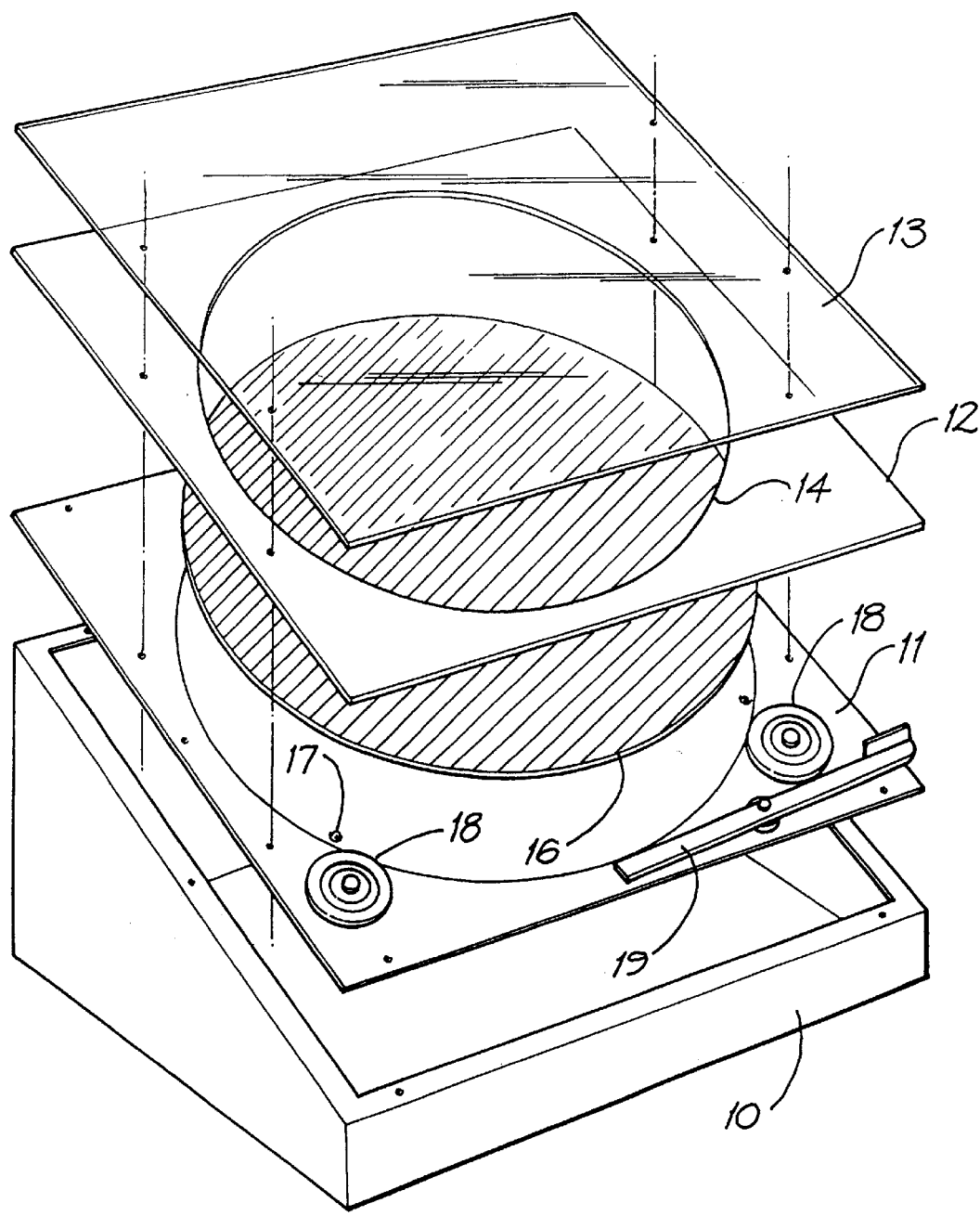
FIG. 2 is a similar view of the apparatus to that as shown in FIG. 1 showing the components in "exploded" configuration for illustrative purposes.

FIG. 2 more clearly illustrates the configuration of the preferred form by showing an exploded perspective view of the apparatus. The elements which have just been described in relation to FIG. 1 are similarly numbered in FIG. 2. This figure illustrates the approximate positioning of a transparency 16 which is in the form of a striated disc and which is positioned to lie on translucent sheet 11 supported by ball bearings mounted in apertures in sheet 11 (only bearing 17 is shown.) Support wheels 18 further assist in the supporting of the striated disc in the apparatus, and the disc is rotated through the provision of an electric motor drive to one of the support wheels through a gear box (See FIG. 3).

FIG. 2 also illustrates ejection arm 19 which is operable to engage disc 16 to enable it to be partly ejected from the apparatus thereby allowing manual removal, it being very difficult to remove the disc since it is "sandwiched" closely between sheets 11 and 12. It should be noted that this figure does not include representations of the lighting equipment of the preferred form of the invention, which is illustrated in subsequent drawings.

Figure 3:
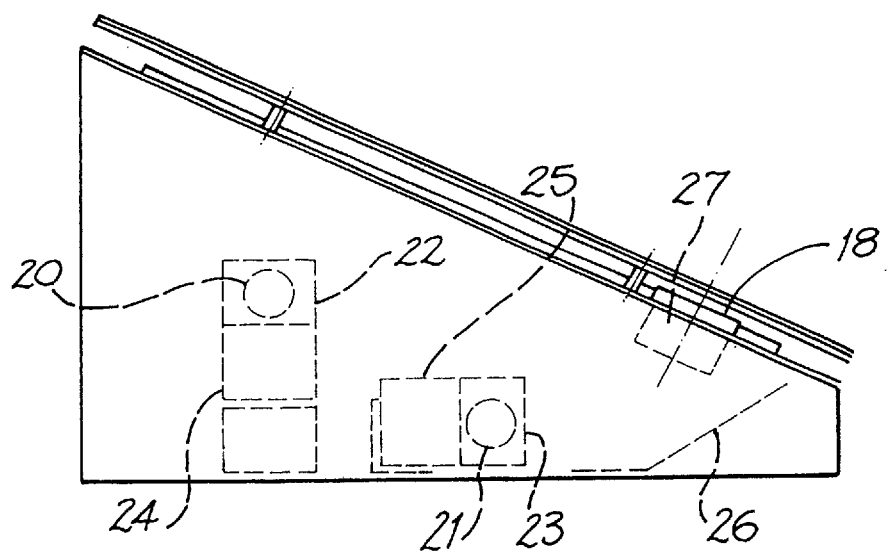
FIG. 3 is an elevation view of the apparatus.

Turning now to FIG. 3, there is shown an elevation of the fully assembled apparatus in which in dotted outline is depicted the position of the two fluorescent tubes 20 and 21 mounted with diffusers 22 and 23 on bases 24 and 25 respectively.

This figure also illustrates reflective surface 26 which is positioned to assist in the provision of a substantially even level of illumination of the striated disc. Motor—gear box combination 27 is shown and is arranged to drive support wheel 18.

Figure 4:
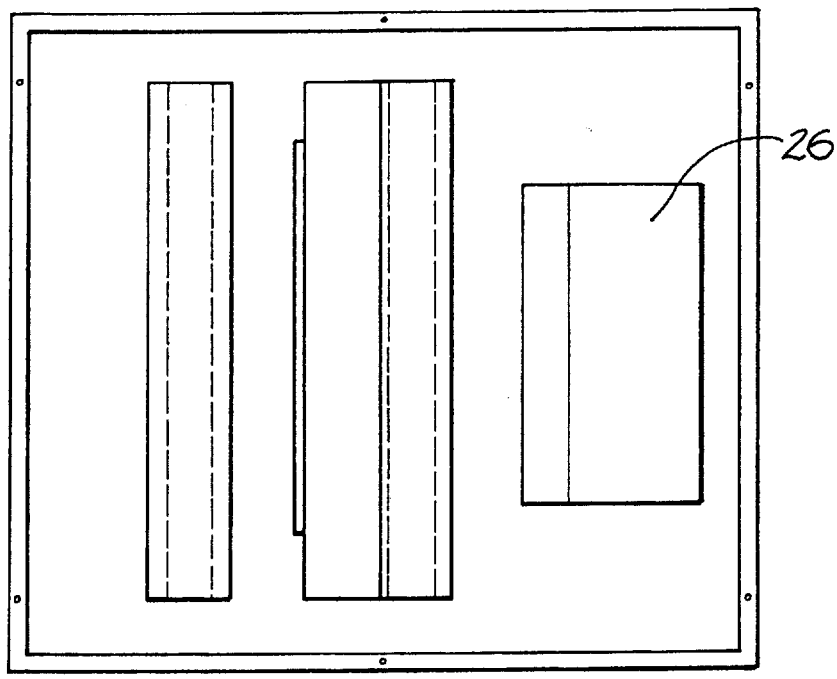
FIG. 4 is a plan view of the apparatus housing with the transparencies and motor drive removed.

FIG. 4 is a plane view of the apparatus housing with the transparencies and motor drive removed. It does provide some further indication as to the layout of the fluorescent lighting tubes and the reflecting shield 26.

Figure 5:
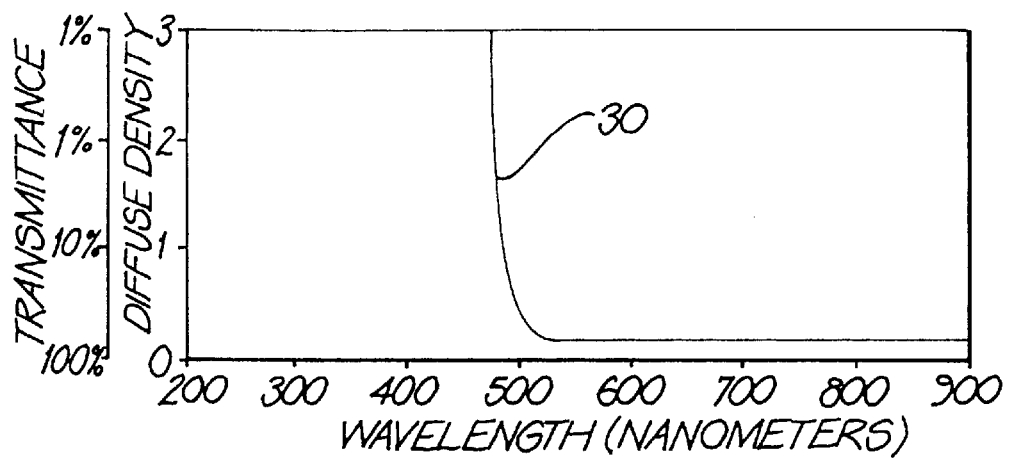
FIG. 5 shows a plot of the filtering effect provided by the preferred "red" filter used as part of the present invention.

FIG. 5 shows a plot of the transmittance of the preferred red filter, which is usable in conjunction with the apparatus as herein defined in the treatment of Dyslexia. The graph is a plot of transmittance against wavelength of electromagnetic radiation and illustrates that electromagnetic radiation of wavelength 500 Nanometers or greater is substantially transmitted (about 95%) by the red filter in question.

Figure 6:
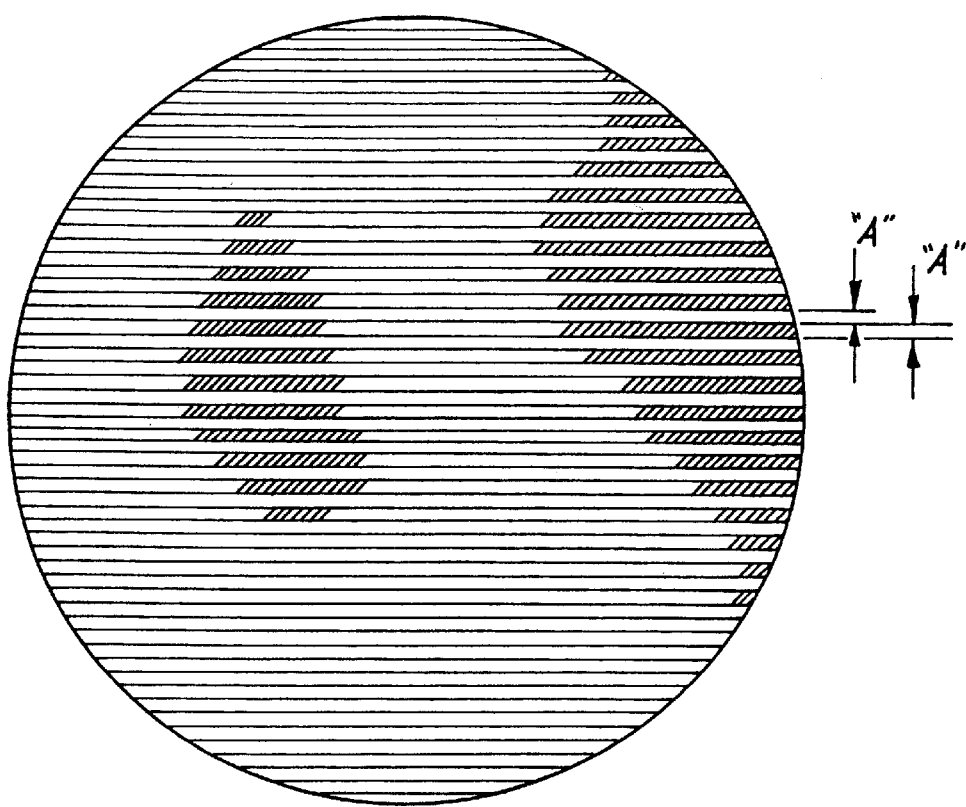
FIG. 6 is an illustration of a transparency suitable for use with the present invention.

FIG. 6 is a transparency useable with preferred embodiment showing opaque stripes of width "A". The width of these stripes preferably ranges from 0.25 to 7 mm. A preferred range of widths is as follows: 7,5,3,2,1, 0.5 and 0.25 mm.

It will therefore be evident that the forgoing describes a method and apparatus for the treatment of Dyslexia which provides for substantially enhanced treatment capabilities.

The preferred embodiment of the method of the present invention relies on seven basic treatment steps of a dyslexic sufferer. The results of treatment via the seven treatment steps have been found to be a substantial reduction in the incidences or affects of dyslexia in patients. The preferred embodiment will be discussed with reference to the treatment of an average 8 year old boy.

It should be initially noted that a very important psychological aspect of the treatment of dyslexia and learning difficulties is that each patient is initially told that it is not their fault that progress in learning has been slow and difficult. They are informed that the underlying problem is based upon the inability of their two eyes to effectively integrate the visual images for prolonged periods of time. A general outline of the treatment should be explained in addition to the likely results. The patient is encouraged to accept responsibility for their own treatment and actively participate in the treatment. The patient should be encouraged and informed that they are a unique individual with special talents and that their learning and study in early years of life are extremely important in allowing them to enjoy a fully successful adult life. Unfortunately, sufferers of dyslexia are often conditioned to failure and they must be made to understand that once the underlying visual problem has been absolved, there will be nothing standing in the way of them participating in a normal life.

The treatment comprises seven main steps and associated homework exercises and requires a number of pieces of equipment for carrying out those steps.

There are supplied seven striped acrylic discs with scientifically graduated frequencies from thick to fine for use in the above described apparatus.

Further, a series of target templates are utilised with the apparatus. The aforementioned target templates normally comprise acetate sheets having various intellectually stimulating puzzles for interaction via a user of the apparatus. Suitable target sheets are hereinafter discussed and are provided in the attached Appendix A to this specification.

Further, water soluble pens of various colours are provided for tracing over the targets by a patient.

Further, there is provided a number of aluminium bars, one approximately 2 cm wide and one approximately 1.7 cm wide.

Further, as will become more readily apparent hereinafter, a opthlamoscope, a red peoptic filter, other eye patches, stereograms, the Worth Titmus test, the Maddox wing test, and a diploscope are provided.

The method of the preferred embodiment of the present invention for treatment of dyslexia relies heavily upon the utilisation of the visual cortex which is located at the back part of the brain. In pure medical terms, it is said to be situated on the medial aspect of the occipital lobe in relation to the calcarine fissure. The visual cortex is characterised by a distinguishable white line or stria of Gennari, which is visible to the naked eye. The cellular structure of the visual cortex is of a highly granular nature as is common in the brain where sensory functions are located. The outer and inner granular layers are made up of small granular cells densely packed together.

In operation, it is thought that the visual cortex operates on the basis of an analogy of a "layered cake" having seven layers. The visual cortex interacts with the eye which behaves in a similar nature to a camera. The apparatus is thought to stimulate the various "layers". The larger banded associated with the apparatus are thought to stimulate the upper layers of the visual cortex and the finer banded discs are thought to stimulate the deepest layer of the visual cortex.

In the method of the preferred embodiment, various further instruments are utilised. Firstly, a diploscope is utilised in later stages of the treatment which involves teaching the highest levels of control of relative accommodation and convergence in the frontal lobe of the brain. The Worth Titmus test is effective in assessing the quality of stereopsis or depth perception. The Maddox rod comprises a rotating prism to measure the degree of horizontal and/or vertical deviations of the visual axis with distance.

The Maddox wing test affords a rapid means for detecting the presence of heterophoria and measuring its degree. A back light and red and green goggles are also suitable for assessing diplopia.

Initial Assessment of the Patient

As noted the method of treatment of the preferred embodiment preferably consists of seven separate sessions which are preferably spaced apart of approximately one hour duration per week. Treatment of patient from e.g. interstate or abroad may alternatively be completed in two weeks, with 5 hourly treatments a week and a total of 10 treatments. Conversely, it is unwise to lengthen the period between treatments to more than 1 week. If e.g. the period was lengthend to 2 weeks, there would be some dissapation of the effects which would in turn require more treatments and make the over all treatment period even longer.

Initially, each eye is examined with a opthlamoscope to ensure that there is no pathological problem existing. If such a problem is detected, the patient should be referred to an ophthalmic surgeon.

A check is made of the aiming point of each eye of the patient. The check should be for a steady binocular fixation. However, many times the fixation of one macular is unsteady or there may be an eccentric fixation. It is suspected that this problem is a significant cause for the learning problems associated with dyslexia in that the patient may be able to obtain a clear focus at any level of gaze but cannot maintain the fixation for a long period and therefore the patient's concentration is liable to lapse. Further, as a result of unsteady or incorrect fixation, it is thought that the frontal lobe of the brain causes deep central suppression of the visual cortex (occipital cortex) of the affected eye thereby accentuating the problem. The deep central suppression of the visual cortex can be treated by the use of the apparatus. The apparatus stimulates the population of visual neurones in the visual cortex by presenting a range of normally seven different spatial frequency gratings, revolving through 360° at a speed of approximately one revolution per minute.

The eccentric or unsteady central macular fixation can be treated by applying a pleoptic red filter in front of the affected eye, while the eye with the central macular fixation is simultaneously patched. Preferably, the internal diffused lighting is even all over in the surrounding environment of the patient, presenting no possible problems with reflected light images. The patient can then view various coloured "targets" of Appendix A preferably rendered in the colours green, blue and black through a pleoptic red filter. The patient's concentration is preferably gained through the utilisation of various puzzles, for example, word games, maths games, sequencing numbers, letters etc and other games. The use of the red filter is a result of the macular being particularly sensitive to red wavelength. It usually takes 3–4 treatment sessions for steady central fixation at the macular of the effected eye to be achieved.

By utilising a opthlamoscope, when the patient has been found to have a steady bi-macular fixation, the normal binocular reflexes can be trained. Work can then be continued on the machine with the full range of coloured "targets", stimulating the full body of the cone receptor cells within the eye, progressing through all the discs to the finest disc. The puzzles and various tasks associated with the "targets" encourage high intellectual stimulation.

Preferably, the work conducted within this and each subsequent session is supported by structured home exercises which become progressively more difficult. In practice, the magnitude and rapidity of the visual recovery by the patient is such that a lasting cure for dyslexia is often achieved after only 7–8 treatments. The treatments typically last for a one hour duration per week. After experiencing the treatment, patients were generally found to have a higher standard of focusing than the average person. The visual acuity was often found to be 6/6 and 6/6 for distance N6 and N6 near or better. The patient has the baility to maintain full dissociation of accommodation and convergence on the frontal lobe of the brain, i.e. controled under the power of the will. Therefore a higher quality of control of the eye than the average person would have has been established for life, giving hightened concentration and a lasting cure.

It is assumed that each of the patient's visits takes place in an orthoptist's clinic. For the purposes of discussion of the preferred embodiment, we will assume the patient to be a child accompanied by a parent as is the normal scenario. Upon arrival for a first appointment, the child is preferably seated by a desk and the parent accommodated close by. Preferably a discussion is had with the child and parent to put them at ease and the patient's history is taken. It is important at this stage for the orthoptist to induce a sense of confidence, concentration and cooperation and, preferably, the orthoptist explains the objective of the session which is to train the brain to produce an effect in the eyes and to coordinate the eyes correctly at every level of gaze from the very far to the very near and to train the brain to interpret correctly what has been seen.

Further, the patient's history could include the derivation of standard factors associated with dyslexia and detailed history taken of the symptoms of dyslexia present in the patient's lifestyle. Further, a normal orthoptist's examination is made of the patient's general demeanour.

A cover test is then carried out to test the near and far fixation. Firstly, the far test is performed by fixation on an object, preferably 20 feet away, with or without glasses. For the near fixation, the patient is asked to fixate on a pencil, torch or stick with a picture sticker or the like which can be moved around, in the normal manner, to ensure proper fixation. This test is done to detect the presence of the strabismus or squint to determine the relevant type etc. Secondly, the test is done to note the presence of any heterophobia. By covering the first eye and then the second eye, with the patient fixating on a pen, torch or the like, any deviation of the eye under cover is noted. Inward deviation normally signifies esophoria, outward deviation normally signifies exophoria, upward deviation normally signifies hyperphoria, downward deviation normally signifies hypophoria. Further, it should be noted whether the eye makes an effort to regain binocular fixation when the cover is removed and as to the relevant speed of recovery of fixation. This test should be conducted both with and without glasses.

The eyes can then examined to demonstrate the presence of any muscle weakness or over reaction of the extra ocular muscles, or change in angle, especially height difference. Preferably the test is carried out without glasses.

Next, an objective convergence test is conducted by utilising a fixation stick which is brought in towards the bridge of the patient's nose. The point where convergence fails should be detected and where the image is blurry should also be detected. Further, any involuntary control should be noted. The test should be carried out both with and without glasses.

Preferably, each eye is then tested with and without glasses utilising the well known Snellens Test type at 20 feet. The test being carried out both with and without glasses. Further, the near sight should be tested both with and without glasses for each eye with Jaegar's Test types.

The Maddox rod can then be utilised for the Maddox rod test by darkening the surroundings, asking the patient to look at a spot of light at 6 meters or 20 feet. The rotating prisms can then be utilised in the normal manner, to measure the degree of horizontal or vertical deviation of the visual axis.

The opthlamoscope can then be utilised within the darkened room environment by examining the weaker eye first to check its general state of condition. The back of the eye fundus is then examined to check the aiming point. The patient is asked to look at the star within the opthlamoscope. This test is then repeated looking at the dominant eye. Normally this eye will appear healthy and when the patient is asked to look at a star he/she will be successfully able to accomplish this task. Where the object is of a star type, the orthoptist can normally observe the star superimposed over the macular in the good eye, whereas, in the other eye, the star usually moves about to a position away from the macular or moves across the macular. The patient can then be asked to close their eyes until the colours have receded and turned black and the patient is then instructed to reopen their eye.

Next, the well known Maddox wing instrument is given to the patient and the patient is asked which number the white arrow points to and which red number the red arrow points to and the results noted. The Maddox wing instrument is utilised to provide a rapid means for detecting the presence of heterophoria at reading distances and measuring its degree.

Next, the patient is asked to wear polaroid glasses and a Worth Titmus test is carried out to assess whether the patient observes any depth in the series of plates. This test provides information on the quality of stereopsis that can be observed or appreciated by the patient. It has been found that, in most cases of dyslexia, usually only a gross stereopsis is noted.

Next, the patient is asked to observe a book with average size print for the patient of that particular age. An aluminium bar is held half way between the eyes of the patient and the book which the patient is to read. The patient is instructed to read the book out loud holding their head steady and to stop when his/her eyes reach the point of the book which is blocked by the aluminium bar. The bar is removed once this point is reached and acknowledged by the patient and the patient is asked to continue reading. Any difficulties associated with subsequent reading should be investigated in order to observe their causes.

The results of the tests are then explained to the patient and/or the parent. For example, problems observed during the opthlamoscope examination should result in a referral to an ophthalmic surgeon. Further, difficulties associated with the visual acuity test should result in a referral to an optometrist for glasses.

The tests may show that the patient has a fatigue in focusing of his/her eyes. For example, the opthlamoscope test may reveal that the patient could not aim one of his/her eyes correctly as the star was unsteady away from the macular or that the star constantly moved across the macular whereas the other eye may have been steady. This may result in a combined unsteady eccentric point in the defective eye as the fixation point. It is thought that the macular of each eye has a corresponding point in the grid of the visual cortex and normally a person can obtain a clear steady fixation at any level of gaze and maintain it. However, the patient suffering Dyslexia is using the macular of the non-effective eye with an unsteady eccentric fixation of the defective eye. This implies that the visual cortex does not contain corresponding points. Therefore, a sufferer of dyslexia normally can obtain a clear focus at any level of gaze but cannot maintain this focus for an extended period. He/she normally keeps failing and, when the focus generally fails, the concentration is lost with the consequential social difficulties. Further, it is thought a sufferer's constant efforts to refocus throughout the day can cause fatigue and frontal headache in addition to a buildup of associate frustration and the like.

Patients observing such visual symptoms can be trained to overcome or eliminate these problems. One such form of training will be described hereinafter. Although many variations on this training possible.

In the embodiment discribed hereinafter, treatments are spaced one week apart and include additional "homework" exercises to be carried in the intervening period.

First Treatment Session

In the first treatment session, the clinical operator places a black eye patch over the good eye of the patient. A red pleoptic filter is placed over the affected eye.

The visual cortex is then stimulated by placing the patient in front of the apparatus, utilising the widest band disc (disc number 1) and an acetate sheet containing target 1, the targets being attached as an appendix to the present specification. Preferably, target 1 is provided in the colour green. The patient is asked to complete the puzzle outlined on the target.

The interaction between the target, the apparatus and the visual cortex provides a strong stimulation source. Of course, other suitable forms of targets could be utilised. It is expected that the completion of target 1 will take approximate 7–10 minutes.

At the conclusion of this exercise, the patient is asked to close both eyes and to convey the colours seen with the eyes closed. It is expected that the patient will respond that they can observe the colours green or blue. The patient is asked to keep their eyes closed until they can see the colour black at which time the treatment can continue. It is thought that the colours seen by the patient indicates that a strong stimulus to the visual cortex has occurred. After a short rest, the colour dissipate to black.

If the patient notices that the bands within the rotating disc "rise" high above the grid that the patient is working on, this is normally an indication of sensory overload and that the patient should rest before continuing. The next target, target 2 which includes a blue maze with green icons and writing can then be utilised as the second target test. Upon completion, which is expected to take approximately 7 minutes, the patient is again asked to close their eyes to rest the eyes. The resumption of the treatment only takes place once colour has disappeared with eyes closed.

Next, the apparatus is utilised with disc number 1 and target 3. Importantly, target 3 comprises a mixture of blue and red lettering. The grid of letters is all in red except for an outer border which comprises two colours, a blue outer most outline and a red inner outline. The heading portion entitled circle a word is preferably printed in blue. As the patient is still wearing a patch over the good eye and a red pleoptic filter over the affected eye, this exercise is often quite difficult. The patient is trying to see red letters through a red filter which takes a great deal of concentration. This test concludes the exercises associated with the first treatment session.

Homework Aids for First Treatment Session

As a first homework exercise, the patient is instructed to wear the red patch over the affected eye whilst the other eye is occluded with a black patch and to watch television programs for about half an hour in the morning and half an hour in the afternoon or evening. The wearing of a red filter ensures that fixation must occur by the affected macular which will be stimulated by the movement of the television image. Further, fixation is further drawn into the central fovea area of the macular, as this area is sensitive to red wavelengths.

A further exercise, denoted the "Union Jack" muscle exercise is performed once a day, at any time of the day. This exercise is directed to strengthening the outside muscles of the eye. In this exercise, the patient is requested to sit on a chair while the parent or friend holds the head firmly with the eyes in a normal "straight ahead" position. Utilising a brightly coloured pen, the patient is then requested to follow the pen with their eyes, six times to the extreme left (west) and then back to the extreme right (east). After completion of the six movements, the patient is to close their eyes and count slowly to 6. It is important that the patient closes their eyes after each set of six movements as the muscles are being used to there extreme limits and the subsequent resting reduces the risk of muscle spasms. Next, the same procedure is repeated in up (north) and down (south) movement. Then oblique movements are utilised from north west to south east and south west to north east.

The next homework exercise is designed to improve a patient's spelling capabilities. It is thought that a patient suffering from dyslexia often has a weak memory retention system, due to the fact that they cannot maintain a steady fixation and that, as the fixation fails, they in turn quickly lose concentration. Hence, when learning to spell, it is thought that they cannot see the pattern of letters for long enough to retain them. Therefore, improvements in visual memory can be quickly achieved by teaching a patient to spell correctly.

One form of suitable exercise will now be described with reference to the attached sheet entitled homework exercise 2 contained within appendix B attached hereto which comprises a suitable list of spelling words. The parent or supervisor is instructed to acquire an exercise book and red and blue pen. Preferably, in the patient's home environment, the parent is instructed to begin the spelling exercise by orally repeating the words in the section Year 1 from the list. Preferably, the parent takes 12 words at a time. The patient is instructed to write the words with a blue pen and the parent and child together check the words. Where a word is incorrect, the parent is instructed to put a red line under the corresponding word on the list. This process is repeated until there are six words underlined in red. The parent then, in another portion of the exercise book, preferably in the middle, and utilising a double page spread of the exercise book, rules up four columns on each page, totalling eight columns across two pages. In the first left column, the parent writes the correctly spelt word neatly in red pen. The patient is then instructed to write this word alternatively in blue, red, blue, red etc across the columns.

In order to learn the words, the patient must learn from the left hand column. The process of transcription is undertaken by covering the left column with paper or card, picking up the blue pen, closing the patient's eyes to visualise the word in the requisite colour and then writing the word. This process is repeated, uncovering the left column each time, alternating between colours. The alternation of colours is thought to reinforce the learning by the visual cortex. The parent continues with the list as required via homework exercise over the forthcoming sessions.

Second Treatment Session

In the second treatment session, the apparatus is initially utilised with disc 2 and targets 4–8 are utilised in conjunction with the apparatus.

Initially, a red filter is placed on the stronger eye, while the affected eye remains unpatched. In this way, the affected eye only sees the red letters, dots or numbers in the various targets while both eyes are able to clearly see the black rotating bands of the apparatus and the green/blue or black letters numbers or lines on the targets. Thus, binocular vision is maintained. As each target is changed, the patient is instructed to sit with their eyes shut and observe the colours seen with closed eyes. The patient is told to reopen their eyes when the colours turn to black. Subsequently, the red filter on the stronger eye is checked or adjusted if necessary and work continues with the next target.

With respect to target number 8, the patient observes two sets of patterns on the left of the vertical black line and the patient is instructed to copy on the right of the vertical line the same pattern. The top grid is delineated in the colour red and the bottom grid is delineated in the colour brown. The patient is instructed to scan the lines from left to right and is instructed that the size and spacing of the dots must be as highly accurate as possible. When the patient has completed the first pattern, he/she is asked to assess it for spacing etc. before proceeding with the second line. The central black vertical line acts as a powerful visual cortex antisuppression device as it must be continually crossed as the patient scans from left to right. This exercise is thought to train accuracy and help to develop the visual cortex memory, the judgement of spacing also assists in hand eye coordination and reading orientation.

Next, the patient is asked to read the patterns out loud (filled, unfilled etc). The patient should be supervised to ensure that the correct patterns are read. This should be repeated until the patterns are correctly read. The importance of this exercise is believed to be significant and additional benefit can be had from repeating the exercise under parental guidance at home or the like for different grids and for copies of the same grid. The grids should be prepared by forming the top grid in red and filling in dots at random. The dots and circles on the bottom grid should be filled in blue. Most suitable results have been found when the patient completes at least one sheet per day. Each grid should take no longer than four minutes for a total 8 minute exercise. No patch should be worn when doing this exercise at home. Preferably, the correction process and the reading aloud process is also repeated for both patterns ensuring that the patient repeats what is observed.

Where the patient experiences problems with reversals of letters, for example "b" for "d", "p" for "q" etc, the exercise based on target 8 can be altered to put tails on the circles such that the circles look like "p's" and "q's" or "b's" and "d's". Further, alternatives could be utilised such as the delta symbol or character symbols. Further, musical symbols such as quavers could also be utilised in place of dots.

The next step in the treatment is to teach the patient an awareness of physiological diplopia. This is a normal accompaniment of the binocular vision and can be taught utilising the red and blue pen. The process of diplopia results in objects beyond the point of fixation appearing double because the images of such objects fall on non-corresponding points of the 2 retinae. Similarly, those nearer than the point of fixation also would appear double. A person is not normally aware of the presence of this "introspective diplopia" owing to retinal inhibition. It should be stressed to the patient that a person will only appreciate diplopia or double vision when doing an exercise such the ones hereinafter described.

The exercise can be conducted by holding the two pens close to the patient's nose, the red pen being further away than the blue pen. The patient is asked to look at the red pen and will see two blue pens in front of the red pen. The patient is instructed to count to 5 keeping the red pen clear and steady, then change fixation to the blue pen, seeing two red pens in the background. Subsequently, the patient should count 5 on the blue pen. This combined process should be repeated three times.

The same exercise should then be redone fixating on an object at mid distance. For example, utilising fixation of a door handle from across a room. Holding the red pen at almost arms length in front of the nose and in line with the fixated object, a count to 5 should first be had with the fixation on the door knob and then on the pen. This process should be repeated three times. Next, the process should be repeated for an object at a longer distance, such as a house across the street through a window, holding the pen at arms length. The person should first fixate on the house or distant object, counting to 5 and then change to fixating on the pen for a further count of 5. This process should be repeated three times. It should be stressed to the patient that they should take responsibility for this important exercise and it should be done a number of times per day for a number of weeks so that a condition reflex is developed which becomes very strong.

It has found in practice that, through this exercise, the patient often becomes more aware of utilising both eyes simultaneously. It is thought that, when patients stop utilising one eye, i.e. the affected eye, the patient is unable to maintain a normal steady fixation in the classroom or elsewhere. It is thought that the affected eye is being constantly suppressed by the highest learning centres of the brain and concentration is rapidly lost. By practicing this exercise at near, mid distance and far distances, a good steady fixation has been found to develop at every level of gaze and improved concentration results.

The next exercise is then introduced. In this exercise, a brightly coloured sticker or object is placed on the end of an ice cream stick to make a possible fixation stick. The patient is asked to hold the stick out in line with the bridge of his/her nose at less than arms length and to slowly bring the stick to the bridge of the nose, keeping the stick in as clear as possible focus for as long as possible. When the stick focus doubles, it should be taken to the initial position. This exercise should be repeated three times, and then the eyes rested. This exercise should be done a number of times each day for a number of weeks. It is important to note that the stick should be brought into the bridge of the nose so that the medial rectus muscles are worked evenly. As this is a strenuous exercise, it should not be done more than three times at a single time or else headaches may occur.

Treatment Session Three

In the third treatment session, the disc number 3 is preferably utilised in the apparatus and various puzzles comprising targets 9, 10, 11, 12, 13 and 14 are initially utilised. Target 9 consists of drawings of ships in red and blue colours with yellow box outlines. Target 10 consists of a maze coloured purple with yellow stars and decorations around the maze having a black outline. Target 11 consists of a multicolour tracing with, in the example illustrated, the bears being purple, red, green, brown, blue and yellow. Target 12, 13 and 14 are coloured puzzles being multicoloured puzzles as illustrated by target 11.

Preferably, a red filter is placed on the strong eye while the affected eye remains unpatched. As each target is changed, the patient is again instructed to sit back and shut their eyes until they see black. Each exercise should take approximately 7 minutes. If necessary, the patient may take a break after completing target 12.

At the conclusion of the apparatus work, the room is darkened and the opthlamoscope is utilised to examine the fundus of each eye. The affected eye is examined first with the patient instructed to look at the star as previously described. It has been found that, with the method of treatment as aforementioned, the patient is often able to look steadily at the star and count the points, look away and then find it again on the first occasion. The patient is often found now to have a steady central fixation at the macular of each eye. Preferably, the visual acuity is then checked for the near distance with Jaegar types. As the fixation is often now central within the affected eye, it has been found that the visual acuity will often improve to give an excellent reading which may now be equal to the stronger eye (N5/N5). If this is the case, the home exercise of watching television with the red filter over the affected eye and the strong eye fully occluded with the black patch can be discontinued. The "Union Jack" exercise can also be discontinued. In its place, two new exercises can be initiated.

Figure 7:
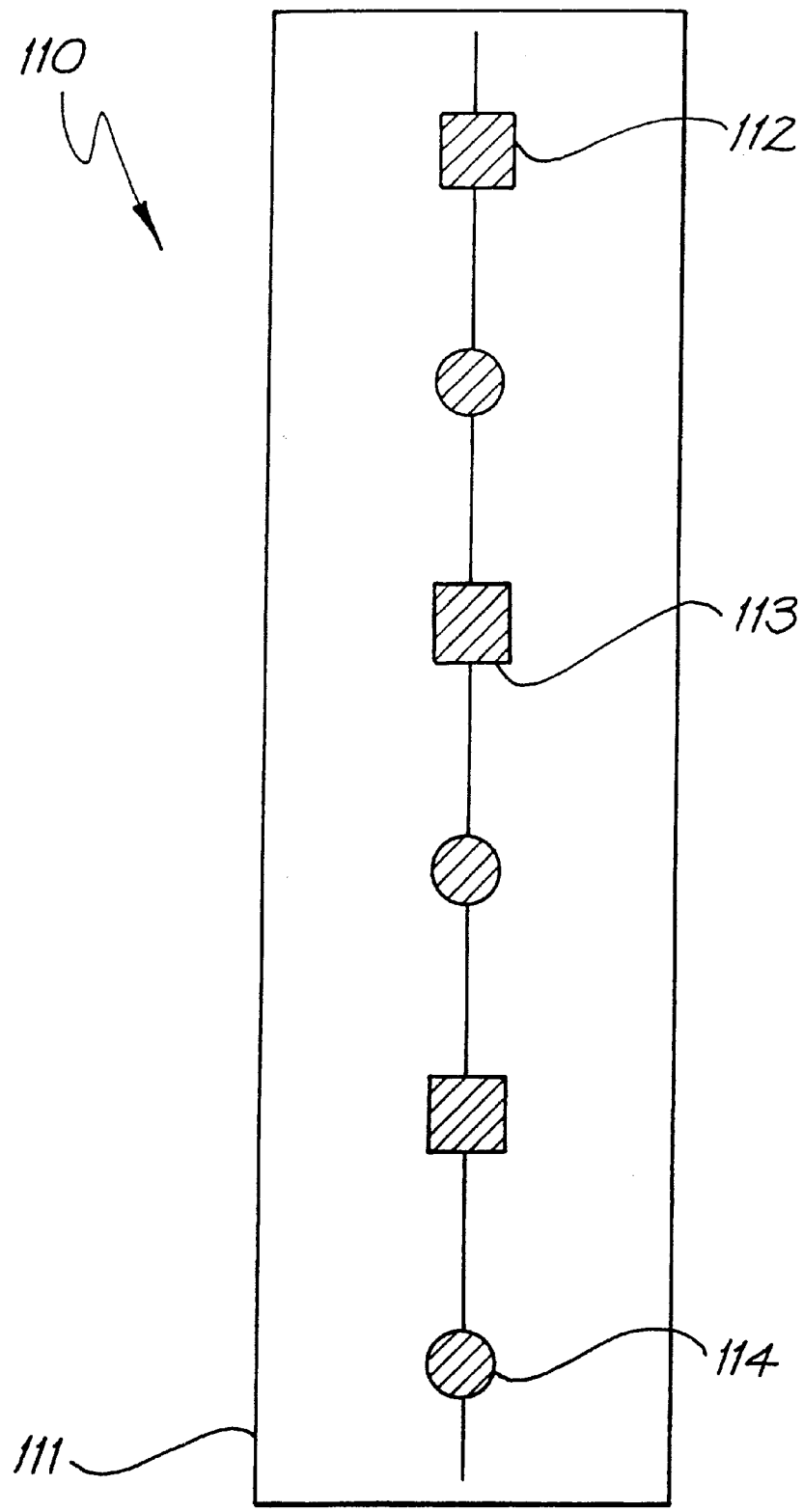
FIG. 7 illustrates forming of a spot card for use with the method of the preferred embodiment.
Figure 8:
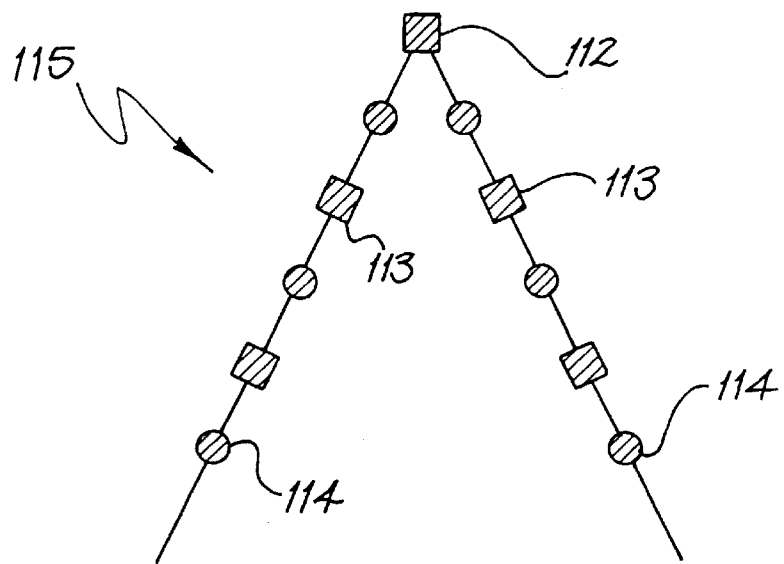
FIGS. 8–10 illustrates various perceived images when utilising the spot card of FIG. 7.
Figure 9:
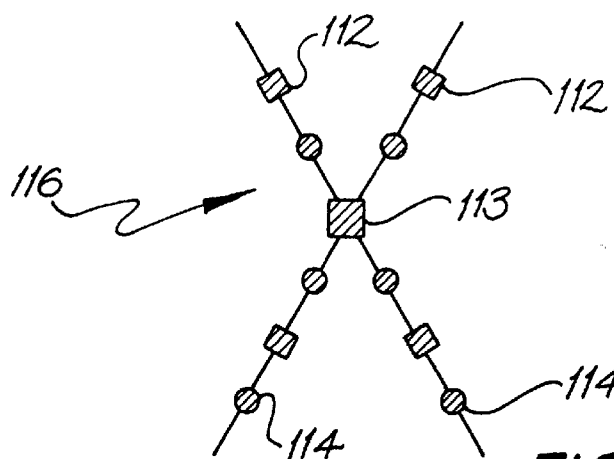
Figure 10:
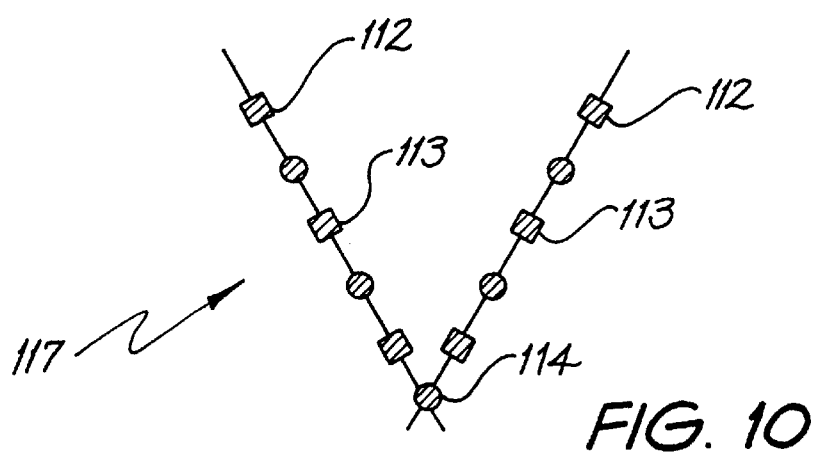

In a first exercise, described with reference to FIGS. 7 to 10, a spot card 10 as shown in FIG. 7 is utilised by the patient. The card is utilised with one end eg 111 touching the nose and held out straight with the black centre line under the bridge, one-third of the way down the nose. The patient is instructed to join the square 112 at the end of the card 110. The image perceived by the patient should be similar to the image 115 as illustrated in FIG. 8. This exercise is based on the physiological diplopia phenomenon whereby objects in front or behind the point of fixation are seen in double. The patient is subsequently asked to join the square 113 and an image similar to the image 116 of FIG. 9 should be observed wherein lines across at point 113. This process is continued down the card, hopefully to the point 114 where the image 117, as illustrated in FIG. 10, should consist of diverging lines. The patient then regresses back down the card to the first position (illustrated in FIG. 8). For practice, the patient should hold each position on the card for a slow count of 7 as he/she moves in and out. The longer each position is held, the stronger the control of relative accommodation and relative convergence in the visual cortex area. Preferably, the spot card exercise is undertaken six times per day. Further, the previous mentioned homework exercise utilising the ice cream stick is continued.

A further exercise introduced in the third treatment, hereinafter referred to as bar reading, can be introduced at this stage as the patient now has a steady bimacular fixation. However, the habit of suppresion of the effected eye still remains. This is well treated by bar reading. It is noted that should the fixation still be unsteady, bar reading, which requires central fixation, would be delayed to a later session.

Figure 16:
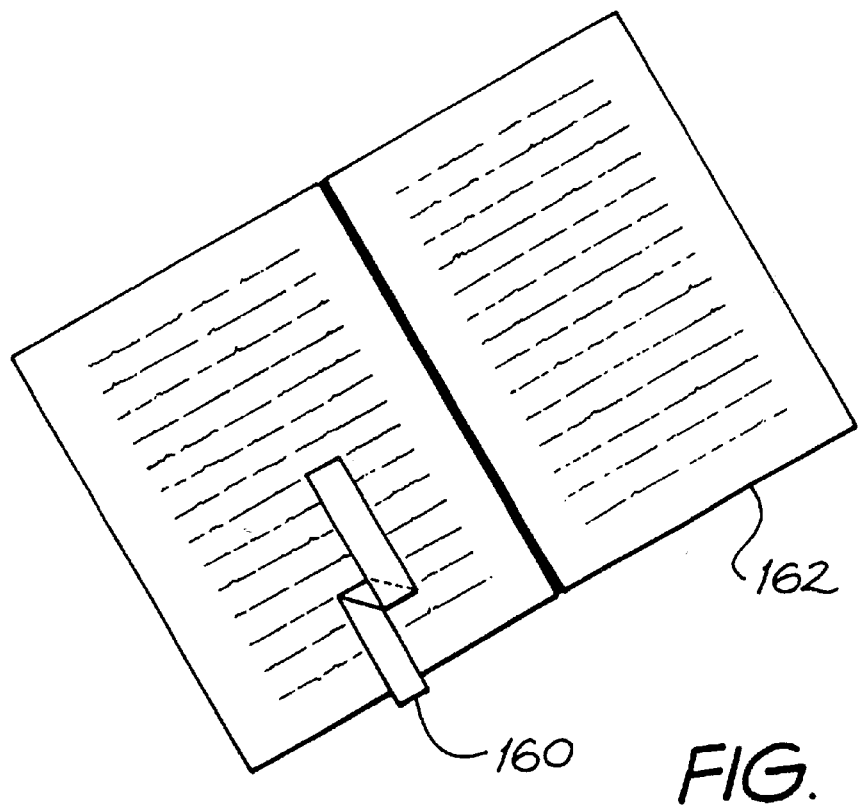
FIG. 16 and FIG. 17 illustrate the utilisation of an aluminium bar to conduct reading exercises in accordance with a method of the preferred embodiment.
Figure 17:
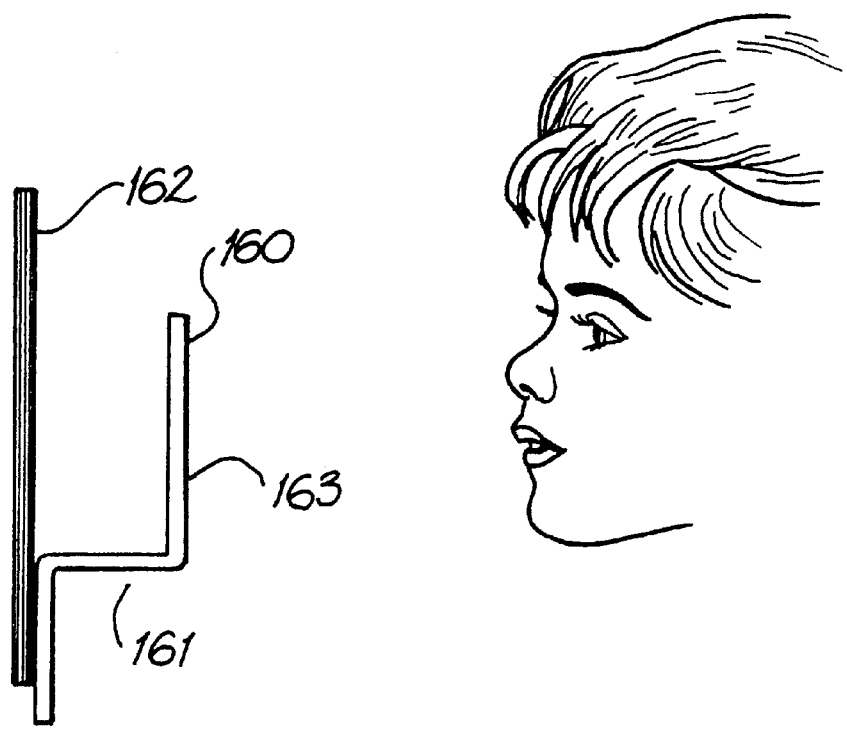

In this exercise, described with reference to FIG. 16 and FIG. 17 the patient is required to hold a aluminium bar 160, approximately 2 cm wide, in front of his nose between his eyes and a book 162. The bar 160 has a portion 161 which is approximately 15 cm long resulting in the bar portion 163 being this distance from the page of the book 162. The bar should be angled so that the thumb of the hand holding the book can secure the bar against the book. Preferably the print of the book should be at least N24 size, much larger than the patient would normally read. The patient is asked to look at a word in the middle of a line and is then asked to read a passage keeping the print quite clear and the spaces between letters and words steady. At some point, the patient may state that the bar blocks out the print and that he cannot read certain portions of the text. This is caused by the habit of suppression from the frontal lobe of the brain into the lower visual cortex. It is thought that this problem arises over time as a bi-product of the condition of fatigue of focus.

The patient is instructed to change his focus to an object, e.g across a room, and then return to the original middle word of the top line. The patient should be able to see the print clearly and the bar should be blurry and in a double image such that the patient can read on from where he/she left of. It is thought that this is a result of the brain becoming irritated by the blocking of the print by the solid bar. Therefore, it is thought that the higher centres of the frontal lobe exert an "overdrive" effect that insists that the images of both eyes be received evenly by the lower cortex in the habit of suppression of the affected eye gets less and less with practice until it is fully eliminated and the print remains clear and steady to the patient's brain. This bar reading is continued as often as possible every day in the normal course of the patient's schooling etc. The more the patient "bar reads" the better his ability to bar read will become. Further, ideally, subsequently the size of the print is reduced to a normal size.

Finally, as a final part of the third treatment, a homework exercise is provided wherein the parent assists in practicing a phonetic sound sheet. The patient is directed to draw up a thin column, initially with the letters A through to Z from top to bottom in the column. Alongside each letter across the page, there is written any words that start with that letter. For example, A may have apple, ant etc. Next, letter combinations are utilised (numbered 27 to 78 of homework exercise 3 as illustrated in Appendix B). This provides more familiarity with various phonetic sounds likely to be encountered in reading.

Treatment Four

At the beginning of the fourth treatment a review of the homework exercises should be undertaken. These include the previously mentioned ice cream stick, the utilisation of the spot card 110 of FIG. 7, and the process of bar reading. Should the bar reading be satisfactory, the print size should be reduced to N12 print and a thinner bar utilised (1.7 cm).

Next, disc number 4 is utilised in the apparatus with targets 15–21 as example puzzles. Each of these puzzles should be formed from multiple different colours with an example colour screen presented in targets 20 and 21.

As with the previous treatments, a red filter is placed on the strong eye while the unaffected eye remains unpatched. The patient obviously reads the directions on each target sheet and writes in the answers etc with a soluble pen on the surface of the apparatus. The turning grid of the apparatus will evolve around the target and stimulate the eyes and brain system, thereby training simultaneous macular perception and strong fusion. After each exercise, which should last approximately 7 minutes, the patient is told to sit back, shut their eyes until the colours have dissipated and they see black. The patient then returns to the machine to work on a new target. The targets should gradually have an increasingly wider colour range to which the patient has to work with.

Next, a homework exercise is set for the next week wherein the patient is required to do a transcription of approximately one page of writing per day. The size of the print to be transcribed should be the normal print size for a particular age. When transcribing, the patient should be informed to concentrate on neatness. Each new line of writing should just touch a red margin ruled down the side of the page and the space between words should be stressed to be even. When transcribing the text, the patient is instructed to read a single word, remember the spelling and write it in full. Subsequently, the patient should remember phrase by phrase and to transcribe a phrase at a time. Preferably, the patient's progress is monitored and in particular, the speed of their work is often found to increase. This exercise helps to establish a conditioned reflex for schooling. The patient's has probably learnt a standard response when work of this nature is required and this exercise assists in overcoming that learned response. The patient's transcription should be closely examined to ensure that the neatness and correctness has been achieved.

We would like the patient to read one sentence at the time visualising it, then write the full sentence without looking back at the text. The writing of the complete thought of the sentence takes the matter deep into the memory. Patient is urged to prcactce this method of transcription—speed and understanding increase markedly.

Treatment Number Five

At the start of this treatment, the homework is examined. In particular, the homework activities associated with target sheet 8 are closely examined. If the patient is achieving well shaped and accurate results, this activity can be discontinued.

Treatment number 5 utilises disc number 5 and targets 22–27 with the apparatus which again comprise multicoloured puzzles. The patient completes the targets while wearing a pair of trial eye glasses each holding plus 10 SP lenses and a pleoptic red lens in front of the stronger eye. The patient then works with targets aforementioned, reading the instructions and writing responses on the apparatus. As previously, when a target is changed, the patient sits back closing his/her eyes until the observed colour has changed to black and then returns to a new task. Half way through this treatment, the lenses may be changed to minus 1 DSP for each eye, keeping the red filter in front of the stronger eye. The patient may observe a blurred print and is encouraged to "clear the print". When this is achieved, the patient is encouraged to continue working.

After completion of the various tasks, the patient is then instructed to complete the aforementioned task utilising the spot card 110 of FIG. 7. If the patient has been suitably practicing in the interim, the patient should have improved to the point where he/she can hold each position in and out of the spot card 110 for a slow count of 10.

Once this is achieved, it is believed that the patient will now have a perfect balance between accommodation and convergence of the eye of minus 10 at 1" meter angle convergence and three dioplers increase in the power of the lens of the eye. This most probably will result in the patient being able to bring his eyes to bear on an object close to the eyes or at infinity or at any point in between and to be able to adjust the eye lens to see clearly. That is, he/she can now maintain a steady focus on any object.

The patient should then be asked to place the line/dot card on its side in front of his/her eyes touching his/her forehead and nose and again to join the last sequence as depicted in FIG. 8, (the card being printed with the same pattern on both sides). The patient is then instructed to join the spots and squares in turn up to the closest position 114 (FIG. 7), holding each for a count of 5, then 7 and finally 10. By putting the card 110 on its side in front of the eyes, it is now impossible for the patient to be fusing images in the normally way. Control of the eyes has therefore been transferred from the lower level of the brain to its higher learning centres. In order to superimpose the images, the patient is required to adjust the convergence and accommodation accordingly within the brain. The patient is instructed to continue to practice this line dot exercise utilising both a flat and vertical card.

The bar reading techniques of the patient are checked and if found to be suitable the print size can be reduced from size N12 to N10.

Figure 11:
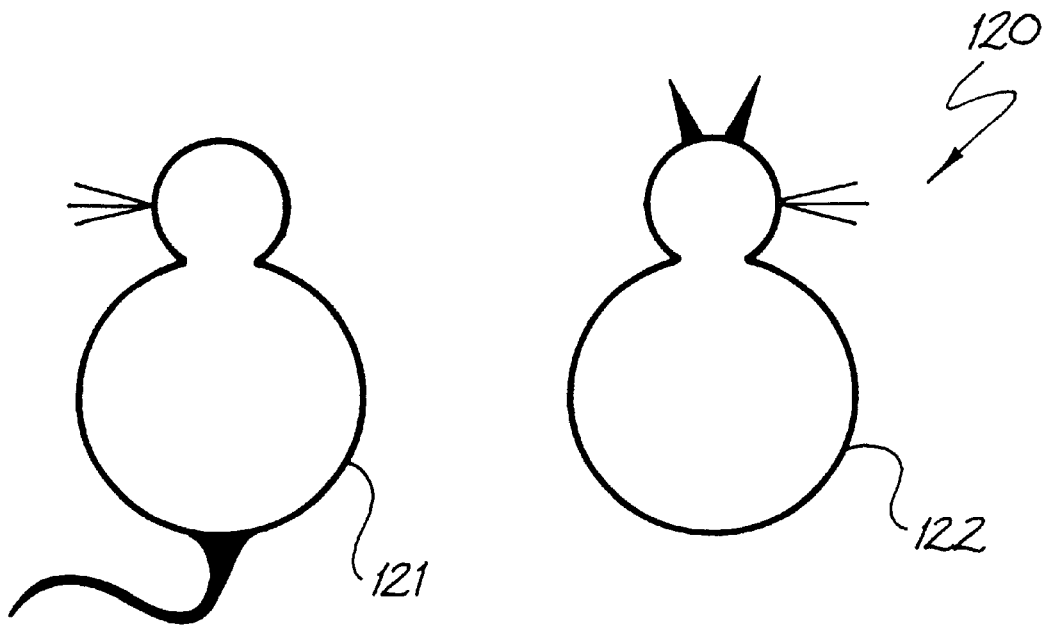
FIG. 11 illustrates a cat card utilised with the method of the preferred embodiment.

Once a patient has reached this stage, it is thought that the patient has established a correct balance between accommodation and convergence. Next, it is necessary to train a disassociation of these two vital functions. The operator places a card with two objects printed on it. For example, the card 120 as illustrated in FIG. 11, having two cats 121, 122 printed on it can be utilised. The card 120 is placed at approximately the patient's reading distance and a pen is held about half way between the card and the eyes. When observing the card, the patient should observe two cats. However, the patient should then be instructed to look at the tip of the pen which should lie on the plane between the eyes and the card. The patient should observe three cats with the middle cat dominating. If part of the middle cat should disappear, this is thought most probably a result of suppression by the visual cortex. With continued mental effort, the concentration will improve the rendering of the middle cat by the brain. Dependence on the pen can then be removed and the patient is asked to hold steady the observance of three cats. Finally, the patient is told to focus on the card so as to see two cats and then, at will, to converge his/her eyes to see three cats with slow counts of 20 in each position.

Next, the cat card 120 is again utilised however, this time fixation is on a distant object, for example, across a room, for example on a door knob. The card is held just under the object of regard at slight relaxed arms length. The distant object is fixated on and the patient again should see 3 cats. The middle cat complete with the controls of ears, whiskers and tail. Concentration is required to maintain the 3 cats and slow counts of 20 are suitable for training, the counts being repeated a number of times. Further, the card exercise should be continued at home.

In utilising the cat card exercise of FIG. 11, it is thought that, in the first position utilising the pen, the patient has to converge his/her eyes on the pen but relax his/her accommodation to see the cat card at the back of the pen. In the second position, the patient is thought to have nil convergence as the visual axis are substantially parallel in observing a distant object. However, the power of accommodation must be increased to see the card in front of the distant object and the situation is reversed.

Initially, this exercise may be difficult for a patient as in normal vision we do not look at something to try and see something else at the same time. However, this exercise is thought to train the frontal lobe with the brain to control the eye so that, in the practice of a series of such exercises, a high standard of focusing is developed.

Treatment Session Six

A review of the progress of the various homework exercise is conducted. Further, a check of the utilisation of the spot card 110 of FIG. 7 is also conducted. Further, a test of the cat card 120 of FIG. 11 is further utilised.

Next, the apparatus is utilised with disc number 6, with targets 28–31 utilised, each of which comprises multiple colours. The colours of particular portions of the target can be varied. One example form of colour is illustrated with target 31.

The patient utilises the apparatus with a pair of trial frames holding a plus 2 DSP lens for each eye. However, in this case the red filter is dispensed with. The number 6 disc comprises very fine lines and target number 28 is initially utilised. Should the patient experience any blurring of print, he/she is encouraged to continue reading until the print becomes clear. After completion of the target, the patient should rest their eyes in the usual manner. Next, target 30 is placed on the machine and minus 2 DSP lenses are utilised. The patient is asked to read the poem carefully, stopping at each stanza to explain the meanings of any difficult words and to explain the general meaning of what has been read. This aids in showing full comprehension of what has been read.

At the end of target 30, the patient should take a break to rest their eyes while target 29 is placed on the apparatus. Preferably, the column of words of target 29 is in blue and the letter grid is in red. The patient is initially asked to read aloud the blue column of words and then to read across the red rows of letters. Subsequently, the patient is instructed to continue with the task, with the words being found by scanning forward, backward, up, down and diagonally within the red letter grid. The patient is encouraged to scan the letters quickly and circle the found words and crossing out each word in the blue column when it is found. Once completed, the patient can move to the "quest" problem with three letter word answers which have to be written in mirror form. After completing this task, the patient should rest his/her eyes. The minus 2 DSP lenses can be removed and plus 3 DSP lenses inserted in the trial frame. Target number 31 is then placed in the machine and the patient requested to read aloud the contents of the target, however being careful to understand the content as he/she will answer the questions noted on the lower part of the target. The patient is then asked to read the across information, which is preferably rendered in red and the down information which is preferably rendered in green. Upon completion of target 31, the lenses and frames are removed.

As in previous treatments, plus and minus lenses of powers 1D, 2D and 3D have been utilised. The minus lens makes the patient accommodate more while the plus lens relaxes the patient's accommodation. The lenses make the print difficult to see so the patient has to constantly adjust his/her eye lens to clear the print to carry out the task. In this way, the utilisation of the various lenses, strengthens the patient's intra-ocular muscles. The lenses utilised give a wide range of control.

Figure 12:
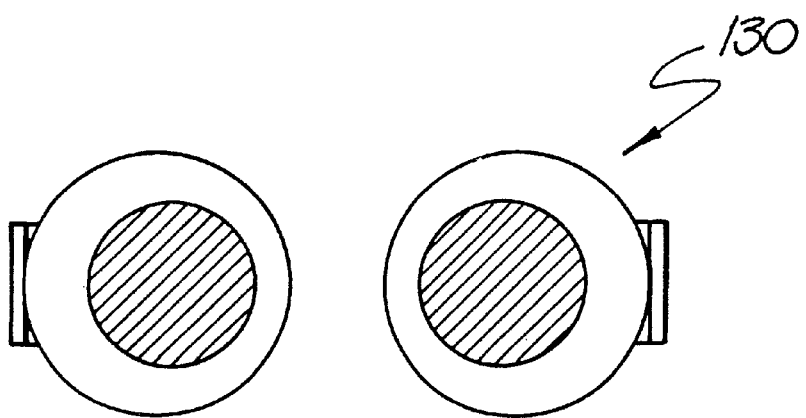
FIG. 12 illustrates a bucket card for use with the method of the preferred embodiment.

Next, a bucket card 130, as illustrated in FIG. 12 is utilised in a similar manner to the cat card 120 of FIG. 11. The patient is asked to converge his/her eyes so as to make three buckets as with the previous cat card exercise. The patient is told to hold the three buckets for a count of 20 and then the distant fixation test is again carried out with the bucket card 130. In the near position the central bucket will look deep, at distance the central bucket is upturned. Referring now to FIG. 13, next an ABC card 140 is utilised in the same manner. The patient should see three lots of three circles with the middle letters and ends clear. The letters A and C in the middle set should rise and the B drop back. This view should be held for a count of 20 and the same procedure repeated with a distant fixation. The central view with a distance fixation is likely to be substantially different with four lots of circles, the middle ones overlapping. It should be seen as three sets of three circles. In the centre set the B circle will rise. Subsequently, a count of 20 can be performed utilising this view.

It is important when utilising cards 130 and 140 that the images are held for a substantial period of time. If they move or disappear, this is thought to be evidence of some remaining central suppression by the brain. With concentration and practice, the images can be held steady.

The final exercise in the sixth treatment is to utilise the card 150 depicted in FIG. 14 which includes two columns of print.

The patient is asked to converge his/her eyes in the normal manner and make three columns of print, then reading it when the print is steady and clear. The card 50 should only be utilised for near convergence and should not be utilised by fixation at a distance.

The various cards depicted in FIG. 11 to FIG. 14 should, as a homework exercise be practiced 3 or 4 times each day with the first three cards being utilised in both near and far positions.

These stereogram cards develop a very high standard of control and amplitude of both accommodation and convergence of the frontal lobe of the brain. Also, a high quality of stereopsis or depth perception will be learnt.

Patients utilising these exercises often, at this point, find that they improve substantially at visual games such as cricket or tennis. Whereas before they would often "lose the ball", they discover that this is often no longer the case.

Further, it is thought that the utilisation of the apparatus assists in preparation of the patient in effectively utilising the cards of FIG. 11 to FIG. 14.

Next, the patient's bar reading abilities should be checked by reading a paragraph of size 10 print utilising a thin bar. If the reading is successful, the print size should be moved to size 8 print and if further successful, the print size should be moved to size 6 print. Further readings should occur at size 6 print as a homework exercise.

In order to improve fluency of reading, a further homework exercise is set wherein the patient is instructed to record his/her reading. The patient should be instructed to utilise the bar reading and recording a paragraph at a time, rewinding the tape and listening the tape. Paragraphs should be re-read until all mistakes etc have been overcome and the paragraph is fluently read. Further, the same passages are also recorded by a parent or the like whose voice the patient is familiar with. This increases the general familiarity of the oralisation of passages of text and has been generally found to improve a patient's oral reading ability. Further, exercises in increasing vocabulary are also beneficial. This can comprise utilisation of a "dictionary notebook" to note new words. The new words should be written in red in a first column one under another and the meaning written in blue to the right of the first column. Each word and meaning should be separately underlined. Importantly, as a homework exercise, the patient should spell the word and read the meaning each day of the week and then use these words in speech and in writing generally.

As a further beneficial exercise, a passage, such as the Kippling poem of target 30 should be neatly transcribed and learnt and discussed.

Treatment Session Seven

At the beginning of treatment seven, the usual review is conducted on the homework material covered in the previous sections. This should include a general discussion of the spelling homework, the reading and tape playback, and the various stereogram cards.

Next, treatment is continued with the apparatus utilising disc number 7 and the accompanying targets 32–35. Each of the targets being of a multicoloured format. The target 32 is initially loaded into the machine and the patient asked to complete the puzzle without any lenses or filters placed in front of the eye. Once finished, the patient should close his/her eyes until the eyes observe black.

Next, target 33 is loaded and the patient instructed to trace over the higher lines on the depicted stereogram. Next, after resting, target 34 is loaded. This target comprises four printed blocks containing nonsensical phrases which are to be scanned. The patient is instructed to scan through the characters and repeat them out loud and then to rest.

The final target, target 35 comprises an exercise in symmetry. The instructor should explain symmetry to the patient by means of the various images and is asked to complete the various disclosed exercises.

Next, the patient is tested with a stereogram, such as that depicted in FIG. 15, which contains two blocks of very fine print. The patient is asked to make three blocks of print utilising eye convergence. By doing so, the patient will be able to read the middle block of print.

Next, the patient is checked with a Maddox wing which invariably gives an orthophoric, normal or slightly esophoric reading illustrating an improvement in muscle tone. The height of the reading is invariably also normal. This instrument is designed to measure the exact position of the eyes at the reading position when fusion is broken. Therefore, the eyes are perfectly aligned at the reading position in this case. The Worth titmus test is then done to assess the gross, medium and fine stereopsis or depth perception, with the patient wearing polarised glasses. A diploscope should then be utilised to show the amount of control the patient has developed from the higher centres or frontal lobe of the brain over the functions of accommodation and convergence. Subsequently, the Maddox rod test should be utilised with patient looking at a spot of light at approximately 6 meters in a darkened room. The patient should be able to see a vertical red line cutting through the spotlight and subsequently a horizontal red line. This evidences simultaneous macular perception with perfect alignment of the eyes at distance.

Next, in a darkened room, a opthlamoscope should be utilised to check the eyes are healthy and the patient is asked to look at the star which can be invariably fixed readily in each eye. Subsequently, the patient is asked to rest his eyes.

Next, a Snellen's test type should be read at 6 meters. Followed by a Jaeger type test with eye patched in term. Subsequently bar reading should be conducted with a small (N6) size print followed by a (N5) size print.

Finally, to check that the eyes are perfectly aligned for the far distance, the patient could be instructed to observe an object at a distance, such as a church steeple placing a tube about 13 inches long, up to his eye while shutting the other eye. He should then place his/her free hand against the tube, palm facing the closed eye. He/she should then open both eyes. The patient should observe the church steeple in a hole in the centre of his hand. This is a result of simultaneous macular perception, as each eye sees a different image and the fusion hold is broken.

It has been found that, by carrying out the aforementioned program, the symptoms associated with dyslexia are most often eliminated.

Of course, many variations of the aforementioned preferred embodiment may also be effective in eliminating the effects of dyslexia.

It would be appreciated by a person skilled in the art that numerous variations and/or modifications may be made to the present invention as shown in the specific embodiments without departing from the spirit or scope of the invention as broadly described. The present embodiments are, therefore, to be considered in all respects illustrative and not restrictive.

For example, it will be appreciated that the apparatus used for the treatment described herein can be replaced if the technology is extended to computer form or virtual reality form.

I claim:

1. A method for treating Dyslexia in a patient, the method comprising the steps of employing techniques to achieve a stable fixation of both eyes, and employing techniques to strengthen the magnocellular visual pathways of the patient, wherein a series of visual image exercises is used for the achieving of the stable fixation of both eyes and the strengthening of the magnocellular visual pathways of the patient and wherein said visual images comprise one or more movable series of high frequency striations interposed with a visual work exercise exercising the patients mental faculties.

2. A method as claimed in claim 1, wherein said visual work exercise comprises on of a puzzle, a story or a drawing.

3. A method as claimed in claim 1, wherein said visual work exercises are of increasing mental complexity.

4. A method as claimed in claim 1, comprising the step of occluding one of the patients eyes during said visual image exercise.

5. A method as claimed in claim 1, comprising the step of colour filtering the light transmitted to the patients eyes during said visual image exercise.

6. A method as claimed in claim 1, wherein said filtering comprises red filtering the light.

7. A method as claimed in claim 1, comprising the step of employing techniques to force the patient to utilise the magnocellular visual pathways in escalating degrees of difficulty.

8. A method for treating Dyslexia in a patient comprising the step of stimulation of the higher visual centres of the brain so as to achieve bimacular fixation, by means of a series of high frequency striations interposed with a visual work exercise exercising the patients mental faculties.

9. A method for treating Dyslexia in a patient comprising the step of:

utilizing one or more moveable series of high frequency striations to stimulate the visual centres of the brain so as to help stabilize the unstable focus of one eye of the patient.

10. A method as claimed in claim 9 wherein a visual work exercise intended to exercise the patient's mental faculties are interposed with the one or more moveable series of high frequency striations so as to strengthen the magnocellular visual pathways of a patient.

11. A method as claimed in claim 10 wherein said visual work exercise comprises one of a puzzle, a drawing or story.

* * * * *